(12) United States Patent
Govari et al.

(10) Patent No.: US 9,713,435 B2
(45) Date of Patent: Jul. 25, 2017

(54) CARDIAC MAPPING USING NON-GATED MRI

(75) Inventors: Assaf Govari, Haifa (IL); Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 189 days.

(21) Appl. No.: 13/191,867

(22) Filed: Jul. 27, 2011

(65) Prior Publication Data
US 2013/0030280 A1    Jan. 31, 2013

(51) Int. Cl.
A61B 5/055    (2006.01)
A61B 5/042    (2006.01)

(52) U.S. Cl.
CPC ............ *A61B 5/055* (2013.01); *A61B 5/0422* (2013.01)

(58) Field of Classification Search
CPC ...................................................... A61B 5/055
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker et al. |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,456,864 B1 | 9/2002 | Swanson et al. |
| 6,690,963 B2 | 2/2004 | Ben-Haim et al. |
| 6,788,967 B2 | 9/2004 | Ben-Haim et al. |
| 6,889,071 B2 | 5/2005 | Saranathan et al. |
| 6,968,032 B2 | 11/2005 | Mohr et al. |
| 6,968,299 B1 | 11/2005 | Bernardini et al. |
| 7,444,011 B2 | 10/2008 | Pan et al. |
| 2005/0057561 A1* | 3/2005 | El-Din ElShishiny et al. ............................ 345/419 |
| 2008/0058635 A1* | 3/2008 | Halperin ................ A61B 5/055 600/411 |

(Continued)

FOREIGN PATENT DOCUMENTS

| | | |
|---|---|---|
| CN | 101449985 A | 6/2009 |
| DE | 10 2008 022 534 A1 | 11/2009 |

(Continued)

OTHER PUBLICATIONS

Sahn D.J. et al., "Review of New Techniques in Echocardiography and Magnetic Resonance Imaging as Applied to Patients with Congenital Heart Disease", *Heart 86(Supp II)*:ii41-ii53 (Dec. 2001).

Sharif B. et al., "Patient-Adaptive Reconstruction and Acquisition in Dynamic Imaging with Sensitivity Encoding (Paradise)", *Magnetic Resonance in Medicine* 64(2):501-513 (Aug. 2010).

(Continued)

*Primary Examiner* — Serkan Akar
(74) *Attorney, Agent, or Firm* — Notaro, Michalos & Zaccaria P.C.

(57) ABSTRACT

A method includes accepting a plurality of Magnetic Resonance Imaging (MRI) data points of a cardiac chamber, acquired over multiple phases of at least one cardiac cycle. A simulated surface of the cardiac chamber is constructed by processing the MRI data points. Measurements of a parameter, acquired at respective points on a surface of the cardiac chamber, are accepted from an intra-cardiac probe. The measurements are overlaid on the simulated surface constructed from the MRI data points, so as to produce a map of the parameter on the surface.

7 Claims, 4 Drawing Sheets

(56) References Cited

U.S. PATENT DOCUMENTS

| | | | |
|---|---|---|---|
| 2009/0105579 A1* | 4/2009 | Garibaldi | 600/409 |
| 2009/0148012 A1* | 6/2009 | Altmann et al. | 382/128 |
| 2009/0281439 A1* | 11/2009 | Harlev et al. | 600/509 |
| 2011/0137153 A1 | 6/2011 | Govari et al. | |

FOREIGN PATENT DOCUMENTS

| | | |
|---|---|---|
| JP | 2003-509145 A | 3/2001 |
| JP | 2007-503893 A | 3/2005 |
| JP | 2009-537249 A | 11/2007 |
| JP | 2011-120906 A | 6/2011 |
| JP | 2011-128191 A | 6/2011 |
| WO | WO 01/20552 A1 | 3/2001 |
| WO | WO 2005/027765 A1 | 3/2005 |
| WO | WO 2007/137045 A2 | 11/2007 |
| WO | WO 2010/058372 A1 | 5/2010 |

OTHER PUBLICATIONS

Lardo A.C. et al., "Visualization and Temporal/Spatial Characterization of Cardiac Radiofrequency Ablation Lesions Using Magnetic Resonance Imaging", *Circulation* 102(6):698-705 (Aug. 8, 2000).
Extended European Search Report dated Oct. 16, 2012 from related European Application No. 12177979.7.
European Examination Report dated Feb. 3, 2015 from related EP 12 177 979.7.
EP Search Report EP 12 17 7979 Dated Oct. 16, 2012.
AU Examination Report AU 2012203967 Dated May 30, 2014.
CN Search Report CN 201210264600.X Dated Jul. 15, 2015.
CN Office Action CN 201210264600.X Dated Jul. 29, 2015.
AU Examination Report AU 2012203967 Dated Sep. 18, 2015.
EP Examination Report for EP12177979.7 Dated Feb. 6, 2014.
EP Examination Report for EP12177979.7 Dated Nov. 4, 2015.
EP Examination Report for EP12177979.7 Dated Feb 4, 2015.
JP Examination Report for JP 2012-165522 Dated Mar. 15, 2016.

* cited by examiner

US 9,713,435 B2

CARDIAC MAPPING USING NON-GATED MRI

FIELD OF THE INVENTION

The present invention relates generally to intracardiac electrical mapping, and specifically to using Magnetic Resonance Imaging (MRI) data for electrical mapping.

BACKGROUND

A wide range of medical procedures involve placing objects, such as sensors, tubes, catheters, dispensing devices, and implants, within the body. When placing a medical probe fitted with position sensors within the body, a reference image of the body cavity to be treated is presented on a display. The reference image assists a medical professional in positioning the probe to the appropriate location(s).

SUMMARY OF THE INVENTION

An embodiment of the present invention that is described herein provides a method that includes accepting a plurality of Magnetic Resonance Imaging (MRI) data points of a cardiac chamber, acquired over multiple phases of at least one cardiac cycle. A simulated surface of the cardiac chamber is constructed by processing the MRI data points. Measurements of a parameter, acquired at respective points on a surface of the cardiac chamber, are accepted from an intra-cardiac probe. The measurements are overlaid on the simulated surface constructed from the MRI data points, so as to produce a map of the parameter on the surface.

In some embodiments, constructing the simulated surface includes identifying a subset of the MRI data points corresponding to the cardiac chamber, and constructing the simulated surface surrounding the identified subset. Identifying the subset may include accepting user input indicating a point belonging to the subset, and determining the subset based on the user input. In an embodiment, constructing the simulated surface includes applying a ball-pivoting process to the identified subset.

In a disclosed embodiment, the method includes presenting the map of the parameter to a user. In another embodiment, overlaying the measurements includes associating each measurement with a respective location on the simulated surface. In yet another embodiment, accepting the measurements includes accepting position measurements of the respective points on the surface at which the measurements were acquired, and overlaying the measurements includes overlaying each measurement based on a respective position measurement. In some embodiments, accepting the MRI data points includes acquiring the MRI data points in a region-of-interest around the intra-cardiac probe while the probe is present in the cardiac chamber, and constructing the simulated surface includes updating the simulated surface in the region-of-interest based on the acquired MRI data points.

In some embodiments, the parameter includes at least one parameter type selected from a group of types consisting of electrical potential on the surface, contact force applied by the probe against the surface, impedance of the surface, relative propagation time of a cardiac signal, and an ablation parameter.

There is additionally provided, in accordance with an embodiment of the present invention, apparatus including first and second interfaces and a processor. The first interface is configured to accept a plurality of MRI data points of a cardiac chamber, acquired over multiple phases of at least one cardiac cycle. The second interface is configured to accept from an intra-cardiac probe measurements of a parameter, acquired at respective points on a surface of the cardiac chamber. The processor is configured to construct a simulated surface of the cardiac chamber by processing the MRI data points, and to overlay the measurements on the simulated surface constructed from the MRI data points, so as to produce a map of the parameter on the surface.

There is also provided, in accordance with an embodiment of the present invention, a computer software product, operated in conjunction with a intra-cardiac probe and a MRI system, the product including a tangible non-transitory computer-readable medium, in which program instructions are stored, which instructions, when read by a computer, cause the computer to accept from the MRI system a plurality of MRI data points of a cardiac chamber acquired over multiple phases of at least one cardiac cycle, to construct a simulated surface of the cardiac chamber by processing the MRI data points, to accept from the intra-cardiac probe measurements of a parameter, acquired at respective points on a surface of the cardiac chamber, and to overlay the measurements on the simulated surface constructed from the MRI data points, so as to produce a map of the parameter on the surface.

There is further provided, in accordance with an embodiment of the present invention, a method including accepting a plurality of MRI data points of a cardiac chamber, acquired over multiple phases of at least one cardiac cycle. A simulated volume of tissue in a vicinity of an intra-cardiac probe, which is operated in the cardiac chamber, is constructed by processing the MRI data points. Measurements of a parameter of the tissue, acquired at respective points in the vicinity of the intra-cardiac probe, are accepted. The measurements are overlaid on the simulated volume.

In an embodiment, accepting the measurements includes receiving the measurements from the intra-cardiac probe. In an alternative embodiment, accepting the measurements includes receiving the measurements from a MRI system that acquires the MRI data points. In a disclosed embodiment, the parameter includes at least one parameter type selected from a group of types consisting of tissue temperature, tissue elasticity, scar indication and ablation depth. In some embodiments, at least a part of the simulated volume is displayed together with a surface map of the cardiac chamber to an operator.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Various diagnostic and therapeutic procedures involve mapping of the electrical potential on the inner surface of a cardiac chamber. Electrical mapping can be performed, for example, by inserting a medical probe (e.g., a catheter) whose distal end is fitted with a position sensor and a mapping electrode into the cardiac chamber. The cardiac chamber is mapped by positioning the probe at multiple points on the inner chamber surface. At each point, the electrical potential is measured using the electrode, and the distal end position is measured using the position sensor. The measurements are typically presented as a map of the electrical potential distribution over the cardiac chamber surface.

Embodiments of the present invention that are described hereinbelow provide improved methods and systems for intracardiac mapping. Although the embodiments described herein refer mainly to electrical potential mapping, the disclosed techniques can be used for mapping of various other parameters. The disclosed techniques use Magnetic Resonance Imaging (MRI) data that is not gated to the cardiac cycle for constructing a simulated surface of the cardiac chamber in question. Once the simulated surface is available, electrical potential measurements received from the intracardiac probe are overlaid on this surface, so as to produce an electrical map of the inner surface of the chamber.

The simulated surface is constructed by recognizing the volume defined by the non-gated MRI data points, and then identifying the outer surface of this volume. In an example embodiment, the surface is identified using a fast mapping technique referred to as a "ball-pivoting" method. Since the MRI data is used for constructing the simulated surface and not for conventional imaging, it is not necessary to limit the MRI data to a specific phase of the cardiac cycle, i.e., gating is not necessary. The use of non-gated MRI data shortens the acquisition time and therefore produces the simulated surface rapidly.

Moreover, the disclosed methods enable anatomical features, such as the pulmonary veins, to be identified in advance and placed directly into the electrical map. Furthermore, the use of non-gated data may enable distinguishing between moving and non-moving body areas. The movement of body tissue can be used to aid automatic segmentation of anatomical structures.

In some embodiments, the MRI data points are acquired and the simulated surface is updated in real time, so as to cover the vicinity of the present location of the intracardiac probe in the heart. In other disclosed embodiments, the MRI data points are used for constructing a 3-D simulated volume in the vicinity of the present location of the probe. Various tissue parameters can be measured in the vicinity of the probe and then overlaid on the simulated volume and displayed.

System Description

Figure 1:
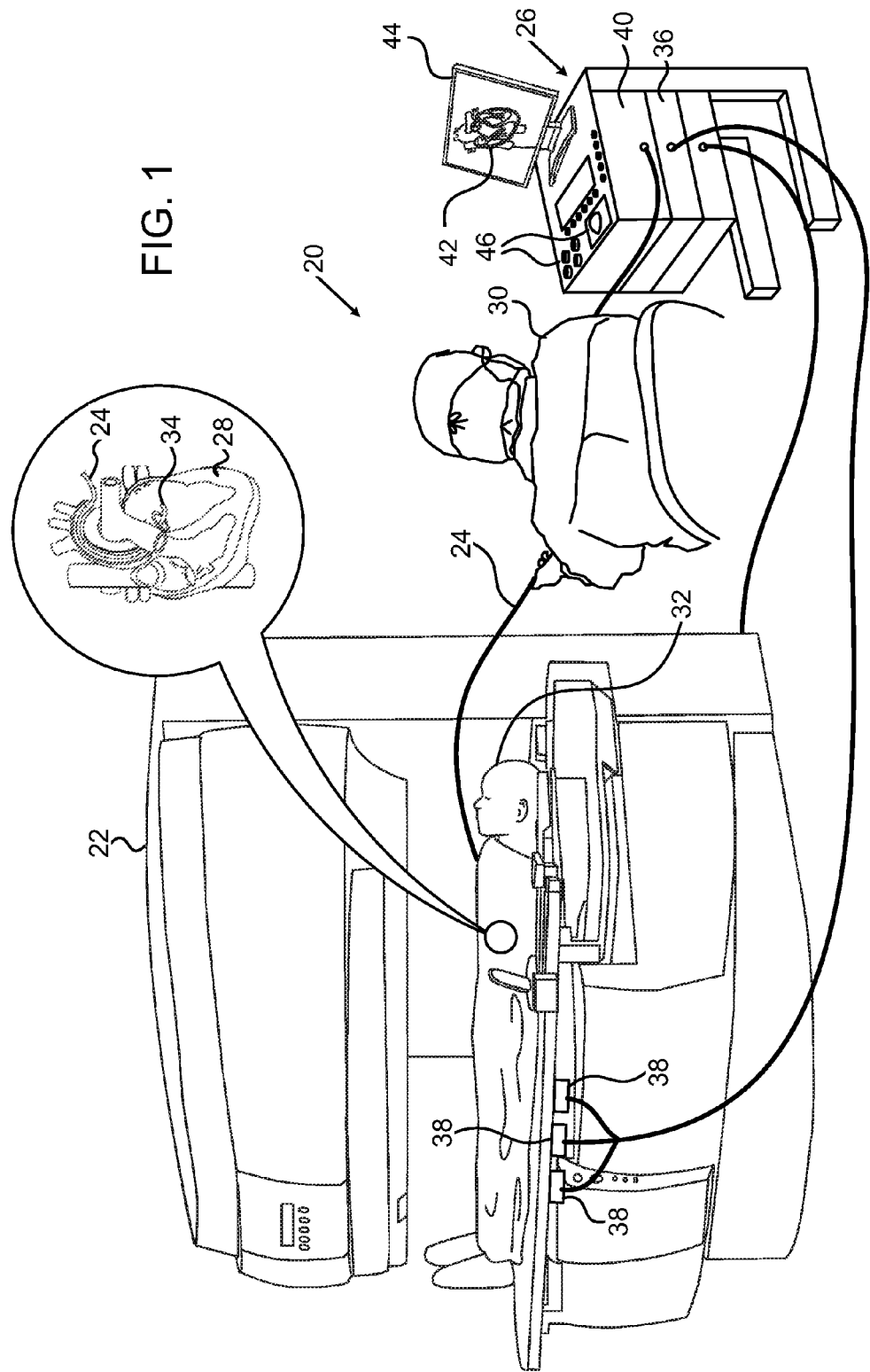
FIG. 1 is a schematic, pictorial illustration of a system for intracardiac electric mapping using non-gated MRI data, in accordance with a disclosed embodiment of the present invention.

FIG. 1 is schematic, pictorial illustration of a system 20 for intracardiac electric mapping using non-gated MRI data, in accordance with a disclosed embodiment of the present invention. System 20 comprises an MRI scanner 22, a probe 24, such as a catheter, and a control console 26. In the embodiment described hereinbelow, probe 24 is used for mapping electrical potentials in a certain chamber of a heart 28 of a patient 32. In some embodiments, probe 24 can be used for additional purposes, such as for performing cardiac ablation. Alternatively, probe 24 may be used, mutatis mutandis, for other therapeutic and/or diagnostic purposes in the heart or in other body organs.

An operator 30, such as a cardiologist, inserts probe 24 through the vascular system of patient 32 so that a distal end of probe 24 enters the cardiac chamber to be mapped. Console 26 uses magnetic position sensing to determine position coordinates of distal end 34 inside heart 28. Console 26 comprises a driver circuit 36 that drives field generators 38, which typically comprise coils placed at known positions, e.g., below the patient's torso. A magnetic field transducer (also referred to as a position sensor—not shown) coupled to distal end 34 generates electrical signals in response to the magnetic fields from the coils, thereby enabling console 26 to determine the position of distal end 34 within the chamber. Although in the present example system 20l measures the position of distal end 34 using magnetic-based sensors, other position tracking techniques may be used (e.g., impedance-based techniques). Magnetic position tracking techniques are described, for example, in U.S. Pat. Nos. 5,391,199, 5,443,489, 6,788,967, 6,690,963, 5,558,091, 6,172,499 6,177,792, whose disclosures are incorporated herein by reference. Impedance-based position tracking techniques are described, for example, in U.S. Pat. Nos. 5,983,126, 6,456,864 and 5,944,022, whose disclosures are incorporated herein by reference.

Operator 30 positions distal end 34 at multiple locations on the inner surface of the heart chamber, where an electrode (not shown) coupled to distal end 34 collects data points indicating electrical potential measurements at the locations. At each location, console 26 measures the position coordinates of distal end 34 using the above-described techniques. The electrical potential measurements are typically correlated with the position measurements.

In addition, MRI scanner 22 acquires MRI data points of the patient's heart 28, or at least of the cardiac chamber to be mapped. The MRI data acquired by scanner 22 is not gated. In the present context, the term "non-gated MRI data" refers to MRI data that is not synchronized or otherwise associated with any specific phase of the cardiac cycle. Non-gated MRI data is typically collected at multiple phases of the cardiac cycle of heart 28, often (although not necessarily) over at least one cardiac cycle. In some embodiments, the MRI data may be gated to the respiratory cycle of the patient.

Console 26 comprises a processor 40, which uses the non-gated MRI data to construct a simulated inner surface of the cardiac chamber in question. Example methods for constructing the simulated surface are described further below. Processor 40 then lays the electrical potential measurements over the simulated surface produced from the non-gated MRI data. Processor 40 displays an image 42 of the simulated surface, with the electrical potential measurements laid thereon, to operator 30 on a display 44. In some embodiments, operator 30 can manipulate image 42 using one or more input devices 46.

Processor 40 typically comprises a general-purpose computer, which is programmed in software to carry out the functions that are described herein. The software may be downloaded to processor 40 in electronic form, over a network, for example, or it may be provided on non-transitory tangible media, such as optical, magnetic or electronic memory media. Alternatively, some or all of the functions of processor 40 may be carried out by dedicated or programmable digital hardware components, or using a combination of hardware and software elements.

Figure 2:
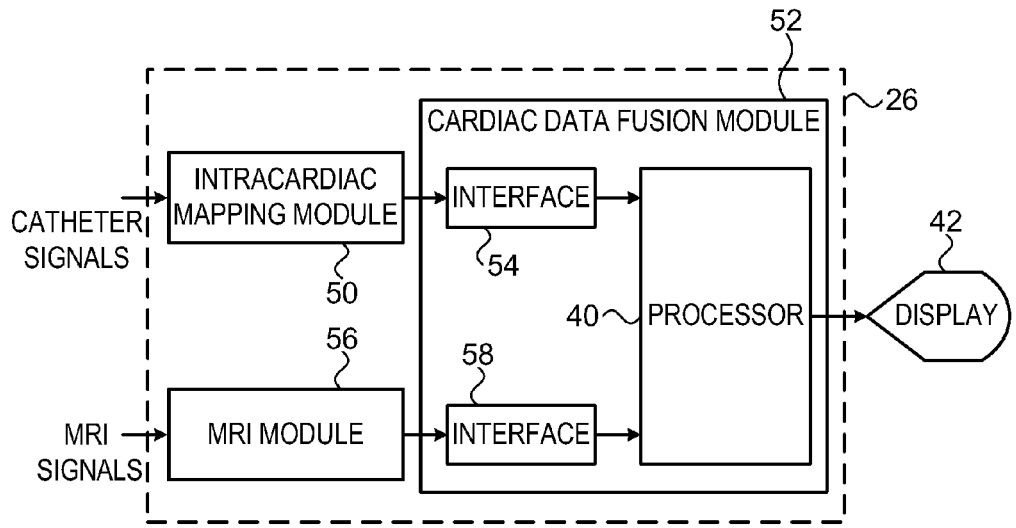
FIG. 2 is a block diagram that schematically illustrates elements of a system for intracardiac electric mapping using non-gated MRI data, in accordance with a disclosed embodiment of the present invention.

FIG. 2 is a block diagram that schematically illustrates elements of console 26, in accordance with a disclosed embodiment of the present invention. An intracardiac mapping module 50 processes electrical potential measurements and position measurements from probe 24, and transmits the collected data points (electrical potential measurements and respective position measurements) to a cardiac data fusion module 52. An MRI module 56 collects the non-gated MRI data from MRI scanner 22 and transmits the data to module 52. Module 52 comprises interfaces 54 and 58 for communicating with modules 50 and 56, respectively. Processor 40 collects the MRI data from interface 58, and applies a fast mapping technique to construct the simulated surface of the inner surface of the cardiac chamber to be mapped. Processor 40 also collects the electrical potential data points from interface 54, and overlays these data points at the appropriate locations on the simulated surface. Processor 40 presents the fused image of the surface and data points on display 44.

Fusion of MRI and Electric Mapping Data

Figure 3:
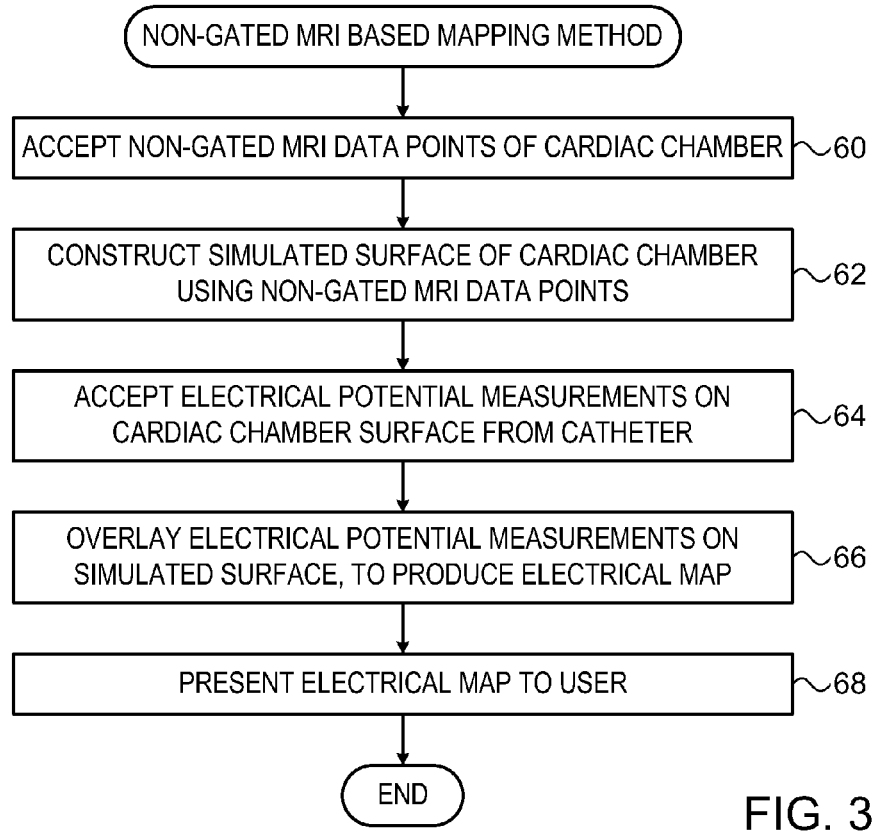
FIG. 3 is a flow diagram that schematically illustrates a method of intracardiac electric mapping using non-gated MRI data, in accordance with a disclosed embodiment of the present invention.

FIG. 3 is a flow diagram that schematically illustrates a method of intracardiac electric mapping using non-gated MRI data, in accordance with a disclosed embodiment of the present invention. MRI scanner 22 acquires non-gated MRI data points of heart 28 over multiple phases of a complete cardiac cycle. Processor 40 accepts the non-gated MRI data points from MRI scanner 22 via interface 54 (step 60). Processor 40 identifies the cardiac chamber to be mapped in the MRI data. In some embodiments, processor 40 presents a three-dimensional (3-D) "cloud" of the collected data points on display 44. Using input controls 46, operator 30 identifies a 3-D region of the cloud representing the chamber to be mapped. Alternatively, processor 40 may identify the volume corresponding to the cardiac chamber automatically or semi-automatically. In an example embodiment, the operator marks a single point that is located in the interior of the chamber. Processor 40 then determines the contiguous volume of the cardiac chamber surrounding this point. At this stage, processor 40 has identified a subset of the MRI data points corresponding to the cardiac chamber of interest. Since the MRI data is non-gated, the identified volume typically represents the cardiac chamber at its largest extent (i.e., during the diastole of the cardiac cycle).

Using a fast mapping technique, processor 40 automatically constructs a simulated surface of the volume, which was identified as corresponding to the cardiac chamber (step 62). As can be appreciated, this simulated surface corresponds to the inner surface (i.e., wall) of the chamber. Processor 40 may use any suitable mapping method for this purpose.

Processor 40 accepts electrical potential measurements acquired by probe 24 at multiple points on the chamber surface (step 64). Processor 40 also accepts position measurements corresponding to the electrical potential measurements. The potential and position measurements are received via interface 54. Processor 40 then overlays the electrical potential measurements on the simulated surface produced from the non-gated MRI data points (step 66). Thus, processor 40 produces an electrical map for the cardiac chamber. The electrical map comprises the simulated surface produced from the MRI data, with the electrical potential measurements overlaid thereon. Typically, processor 40 associates each electrical potential measurement with a respective point on the simulated surface, based on the position measurements that correspond to the electrical potential measurements. For example, processor 40 may associate each electrical potential measurement with the nearest point on the simulated surface. Processor 40 may apply any suitable geometrical adjustment as part of the overlaying operation. Finally, processor 40 presents the electrical map to operator 30 on display 44 (step 68).

Simulated Surface Construction Using Fast Mapping

Processor 40 may apply any suitable method for constructing the simulated inner surface of the cardiac chamber, based on the 3-D "cloud" of non-gated MRI data points. An example process, referred to as a "ball-pivoting algorithm," is described in U.S. Pat. No. 6,968,299, whose disclosure is incorporated herein by reference. The ball-pivoting algorithm constructs a mesh of triangles that interpolates a given point cloud, by "rolling" a ball of radius r on the point cloud. The algorithm starts with a seed triangle, and first pivots the ball around an edge of the seed triangle. During the pivoting operation, the ball revolves around the edge while keeping in contact with the edge's endpoints (i.e., initially two points of the seed triangle). The ball pivots until it touches another point in the point cloud, forming another triangle. The ball-pivoting operation continues until all reachable edges have been tried, and then starts from another seed triangle, until all points in the point cloud have been considered, thereby completing the definition of the surface.

Figure 4:
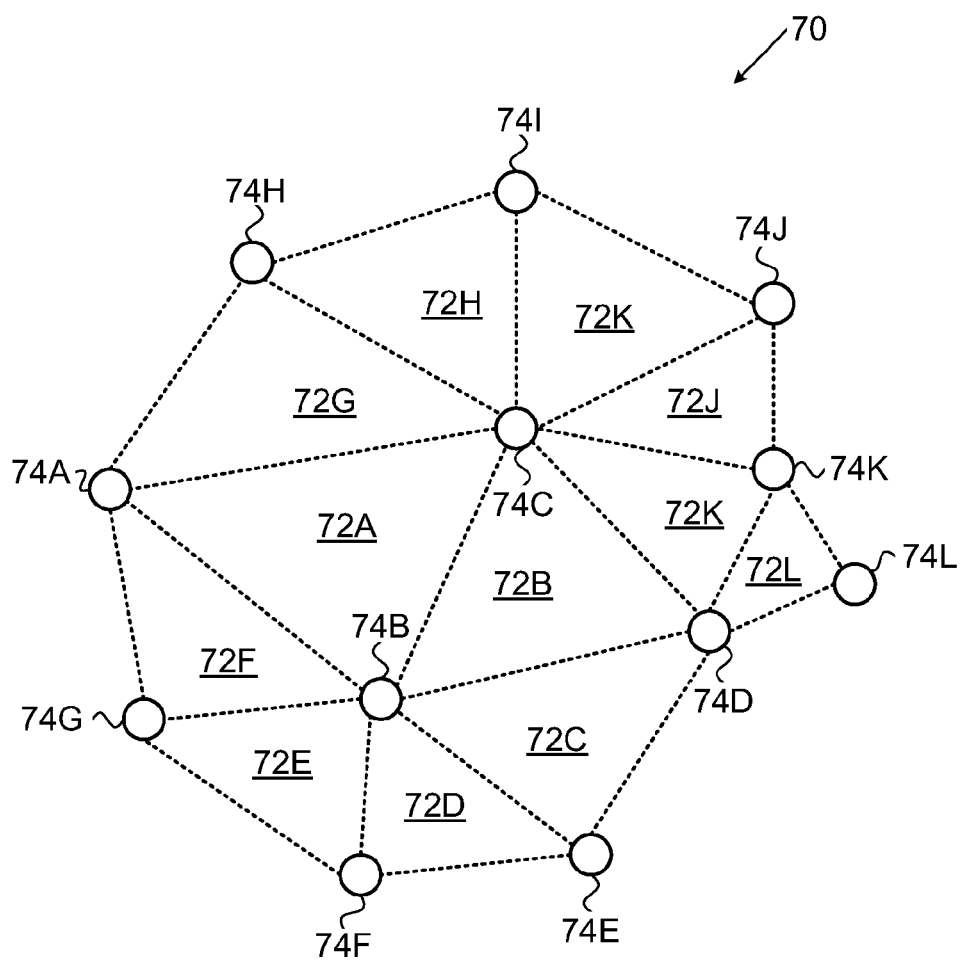
FIG. 4 is diagram that schematically illustrates a process for constructing a simulated surface of a cardiac chamber using non-gated MRI data, in accordance with a disclosed embodiment of the present invention.

FIG. 4 is a diagram illustrating a simulated surface 70 of a chamber of heart 28, which was derived using the above-described ball-pivoting algorithm, in accordance with an embodiment of the present invention. The figure shows only a small portion of the chamber surface, comprising twelve triangles 72A . . . 72L, for the sake of clarity. The twelve triangles interpolate twelve MRI data points 74A . . . 74L. When carrying out the ball-pivoting process, processor 40 first identifies an initial seed triangle 72A whose vertices are MRI data points 74A, 74B and 74C. After identifying seed triangle 72A, processor 40 selects point 74C as an interior pivot point. Processor 40 then pivots the ball along edges containing point 74C, thereby defining triangles 72B through 72F. After defining all the triangles around pivot point 74C, processor 40 then pivots on exterior point 74A, and identifies point 74B as the next interior pivot point, thereby defining triangles 72G . . . 72K, using the method described supra. Finally, processor 40 pivots on exterior point 74D to define triangle 72K. The triangles of surface 70 are defined as follows:

| Triangle | Edge | Points |
|---|---|---|
| 72A (Seed) | None | 74A, 74B, 74C |
| 72B | 72B-72C | 74B, 74C, 74D |
| 72C | 72B-72D | 74C, 74D, 74E |
| 72D | 72B-72E | 74C, 74E, 74F |
| 72E | 72B-72F | 74C, 74F, 74G |
| 72F | 72B-72G | 74C, 74G, 74A |
| 72G (Seed) | None | 74B, 74A, 74H |
| 72H | 72C-72H | 74B, 74H, 74I |
| 72I | 72C-72I | 74B, 74I, 74J |

| Triangle | Edge | Points |
|---|---|---|
| 72J | 72C-72J | 74B, 74I, 74K |
| 72K | 72C-72K | 74B, 74K, 74D |
| 72L (Seed) | None | 74D, 74K, 74L |

Figure 5:
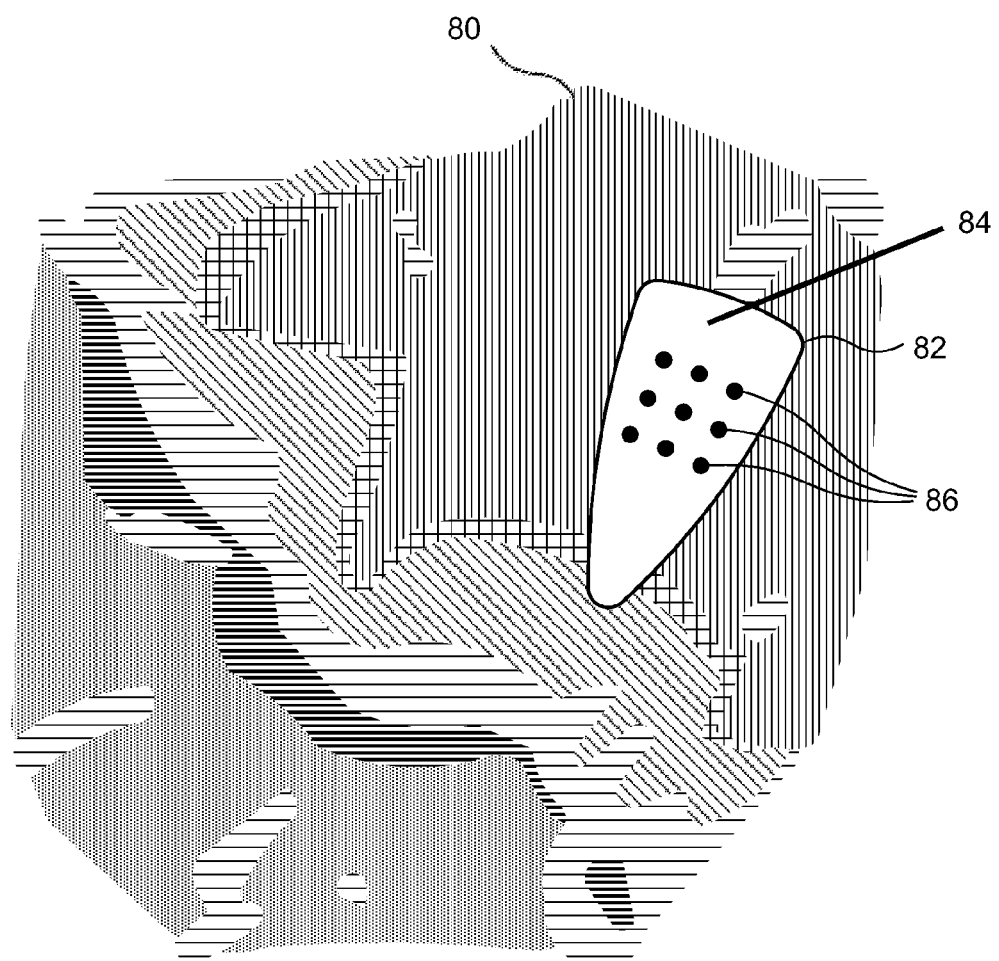
FIG. 5 shows electrical potential measurements overlaid on a simulated surface of a cardiac chamber, in accordance with a disclosed embodiment of the present invention.

FIG. 5 shows an electrical map, comprising electrical potential measurements overlaid on a simulated surface of a chamber of heart 28, in accordance with a disclosed embodiment of the invention. A 3-D point cloud 80 comprises multiple non-gated MRI data points of heart 28, collected during step of the method of FIG. 3 above. Different shading patterns in point cloud 80 represent different tissue types. For example, 3-D regions comprising heart muscle may have different shading than 3-D regions comprising blood (e.g., cardiac chambers).

A region 84 corresponds to a chamber of heart 28 that is selected by operator 30 using input devices 46. A simulated surface 82 defines the inner surface of chamber 84, as generated by processor 40. Data points 86 comprise electrical potential measurements, which were collected and then overlaid on the simulated surface. When presenting the electrical map on display 44, processor 40 pins data points 86 to surface 84 (while possibly applying any necessary geometric adjustments), thereby providing operator 30 with an enhanced visual representation of the cardiac chamber and its electrical activity.

The overlaying of electrical measurements on the MRI-based simulated surface enables operator 30 or processor 40 to identity anatomical features of heart 28 that may be difficult to identify using position measurements alone, e.g., pulmonary veins. These features can be placed directly into the electrical map. Furthermore, the use of non-gated MRI data may enable processor 40 to distinguish between moving body and non-moving body areas in (or near) heart 28. Processor 40 can analyze the movement in the body tissue to assist in automatic segmentation of such areas based on the non-gated MRI data.

Although the embodiments described herein refer mainly to intracardiac electrical potential mapping using an invasive probe, the disclosed techniques can be used in other physiological mapping applications. Alternative parameters that can be mapped, overlaid and displayed using the disclosed techniques may comprise, for example, the contact force applied by the probe against the cardiac chamber surface, the impedance of the surface, the local activation time (i.e., the propagation time of the cardiac signal to various points on the surface relative to some reference point), and/or an ablation parameter. Although the disclosed techniques use MRI data points that are not gated relative to the cardiac cycle, in some embodiments the data points may be gated relative to the respiratory cycle of the patient. Although the embodiments described herein refer mainly to mapping the inner surface of the cardiac chamber, the disclosed techniques can be used for mapping a parameter acquired by a probe that is manipulated on an outer surface of the heart.

In some embodiments, MRI module 56 acquires the MRI data points in real time, as probe 24 moves through a cardiac chamber. The MRI data points are collected in the vicinity of the current location of the probe, and processor 40 updates the simulated surface using these data points. In an embodiment, the overall simulated surface of the cardiac chamber is updated in real time with the acquired MRI data points. Using this technique, operator 30 is provided with an up-to-date MRI image of the immediate region-of-interest around the probe. In one embodiment, the simulated surface and/or the volume encompassed by the simulated surface is displayed only for this immediate present vicinity of the probe. This technique may be used, for example, for detecting tissue change during ablation, and/or for comparing the tissue before and after ablation.

In some embodiments, processor 40 uses the MRI data points to construct, in real time, a simulated volume of the tissue in the vicinity of the present location of the probe. On this simulated volume, processor 40 may overlay measurements of various tissue parameters for displaying to operator 30. Using this technique, the operator is provided with a 3-D map of a certain tissue parameter that is acquired at various points in the volume surrounding the present location of the probe.

Types of tissue parameters that may be acquired, overlaid and displayed on the simulated volume comprise, for example, tissue temperature, tissue elasticity, scar indication, ablation depth, and/or any other suitable parameter. The tissue parameter may be acquired by the probe and/or by the MRI system that provides the MRI data points.

In various embodiments, a 3-D map of the tissue parameter or part of the map may be displayed to the operator alone, overlaid on the simulated volume, and/or together with the simulated surface of the cardiac chamber.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It is intended that the appended claims cover all such features and advantages of the disclosure that fall within the spirit and scope of the present disclosure. As numerous modifications and changes will readily occur to those skilled in the art, it is intended that the disclosure not be limited to the limited number of embodiments described herein. Accordingly, it will be appreciated that all suitable variations, modifications and equivalents may be resorted to, falling within the spirit and scope of the present disclosure.

The invention claimed is:

1. An apparatus, comprising:
 a Magnetic Resonance Imaging (MRI) scanner, which is configured to acquire a plurality of non-gated MRI data points of a cardiac chamber, acquired over multiple phases of at least one cardiac cycle;
 an intra-cardiac probe comprising a position sensor configured to generate position signals used to determine position coordinates of a distal end of the intra-cardiac probe, the intra-cardiac probe configured to acquire parameter measurements of a parameter acquired at respective points on a surface of the cardiac chamber;
 a display;
 a control console which performs the steps of:
  receiving the position signals from the position sensor,
  determining position coordinates of the distal end of the intra-cardiac probe based on the position signals, receiving the parameter measurements of the parameter acquired at respective points on the surface of the cardiac chamber by the intra-cardiac probe, collecting the non-gated MRI data points of the cardiac chamber from the MRI scanner, and transmitting the non-gated MRI data points; and a processor operatively connected to the control console, the processor comprising a computer having tangible non-transitory computer-readable medium, in which program instructions are stored, which instructions, when read by the computer, cause the computer to:

(1) accept the non-gated MRI data points transmitted by the MRI module, (2) identify a volume of the cardiac chamber containing the accepted non-gated MRI data points, (3) construct a simulated surface of the volume and display on the display the simulated surface comprising a wall of the cardiac chamber, (4) accept from the control console parameter measurements of a parameter acquired at respective points on the surface of the cardiac chamber by the intra-cardiac probe and position coordinates obtained by magnetic position sensors, where the position coordinates correspond to the parameters, and associating each parameter measurement with a respective point on the simulated surface based on the position coordinates of each respective point, (5) producing an electrical map of electrical potential measurements of the surface of the cardiac chamber by overlaying the associated parameter measurements on the simulated surface of the volume, (6) update the simulated surface on the cardiac chamber in real time based on the acquired MRI data points and displaying on the display.

2. The apparatus according to claim 1, wherein the processor is configured to identify a subset of the non-gated MRI data points corresponding to the cardiac chamber, and to construct the simulated surface surrounding the identified subset.

3. The apparatus according to claim 2, wherein the processor is further configured to acquire user input indicating a point belonging to the subset, and to identify the subset based on the user input.

4. The apparatus according to claim 2, wherein the processor is further configured to construct the simulated surface by applying a ball-pivoting process to the identified subset.

5. The apparatus according to claim 1, wherein the MRI scanner is configured to acquire the non-gated MRI data points in a region-of-interest around the intra-cardiac probe while the intra-cardiac probe is present in the cardiac chamber, and wherein the processor is configured to update the simulated surface in the region-of-interest based on the acquired non-gated MRI data points.

6. The apparatus according to claim 1, wherein the parameter comprises at least one parameter type selected from a group of types consisting of electrical potential on the surface, contact force applied by the intra-cardiac probe against the surface, impedance of the surface, relative propagation time of a cardiac signal, and an ablation parameter.

7. A computer software product, operated in conjunction with an intra-cardiac probe, a Magnetic Resonance Imaging (MRI) system and a display, the product comprising a tangible non-transitory computer-readable medium, in which program instructions are stored, which instructions, when read by a computer, cause the computer to:

(1) accept non-gated MRI data points transmitted by the MRI system, (2) identify a volume of a cardiac chamber containing the accepted non-gated MRI data points, (3) construct a simulated surface of the volume and display on the display, the simulated surface comprising a wall of the cardiac chamber, (4) accept parameter measurements of a parameter acquired at respective points on the surface of the cardiac chamber by the intra-cardiac probe and position coordinates obtained by magnetic position sensors, where the position coordinates correspond to the parameters, and associating each parameter measurement with a respective point on the simulated surface based on the position coordinates of each respective point, (5) producing an electrical map of electrical potential measurements of the surface of the cardiac chamber by overlaying the associated parameter measurements on the simulated surface of the volume, (6) updated the simulated surface on the cardiac chamber in real time based on the acquired MRI data points and displaying on the display.

* * * * *